(12) United States Patent
Blank et al.

(10) Patent No.: US 9,327,212 B2
(45) Date of Patent: May 3, 2016

(54) METHOD AND SYSTEM FOR PREPARATION OF LIQUID MIXTURES

(75) Inventors: Torbjorn Blank, Uppsala (SE); Enrique Carredano, Uppsala (SE); Karl Ekstrom, Uppsala (SE); Jan-Erik Lynga, Uppsala (SE); Roger Nordberg, Uppsala (SE); Mike Peters, Uppsala (SE); Gustav Rodrigo, Uppsala (SE); Henrik Sandegren, Uppsala (SE); Lisa Stack, Piscataway, NJ (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 578 days.

(21) Appl. No.: 13/497,896

(22) PCT Filed: Sep. 23, 2010

(86) PCT No.: PCT/SE2010/051023
§ 371 (c)(1),
(2), (4) Date: Mar. 23, 2012

(87) PCT Pub. No.: WO2011/037530
PCT Pub. Date: Mar. 31, 2011

(65) Prior Publication Data
US 2012/0217192 A1   Aug. 30, 2012

(30) Foreign Application Priority Data
Sep. 25, 2009 (SE) ...................... 0950703

(51) Int. Cl.
*B01D 15/16* (2006.01)
*G01N 30/34* (2006.01)

(52) U.S. Cl.
CPC .......... *B01D 15/166* (2013.01); *B01F 15/0022* (2013.01); *B01F 15/00227* (2013.01); *G01N 30/34* (2013.01); *G05D 11/132* (2013.01); *G01N 2030/347* (2013.01)

(58) Field of Classification Search
CPC .... B01D 15/166; B01D 15/16; B01D 15/168; G05D 11/02; G05D 11/13; G05D 11/108; G05D 11/135; G05D 11/139; G05D 21/00; G05D 11/132; G05D 11/08; G05D 11/138; G01N 30/34; G01N 2030/347; B01F 15/00123; B01F 15/00129; B01F 15/0022; B01F 15/00227; B01F 15/00259; B01F 15/00272; B01F 15/00279; B01F 15/00285; B01F 15/00292; B01F 15/00207
USPC ............... 210/85, 96.1, 101, 143, 198.2, 656, 210/739, 743; 366/152.1, 152.4, 160.1, 366/182.1; 137/3, 88, 93, 111; 700/239, 700/240, 265, 267, 285; 506/13
See application file for complete search history.

(56) References Cited

U.S. PATENT DOCUMENTS 3,712,513 A   1/1973   Ashmead et al.
4,053,743 A   10/1977  Niemi (Continued)

FOREIGN PATENT DOCUMENTS

WO   WO 97/31692   9/1997
WO   WO 01/06233   1/2001

(Continued)

*Primary Examiner* — Joseph Drodge
(74) *Attorney, Agent, or Firm* — Parks Wood LLC (57) ABSTRACT

A method for preparing a liquid flow having pre-defined characteristics by mixing liquid flows of at least two different component stock solutions with each other comprises the steps of determining a selected property value for one or more of the stock solutions by sensing, in a flow of each stock solution separately, at least one characteristic related to the property value for the stock solution, and based on the determined property value or values, mixing the stock solution flows in mixing ratios giving the desired mixed liquid flow. A system for carrying out the method comprises sensor means and a control unit, wherein the control unit is arranged to evaluate the characteristics sensed by the sensor means and provide relative ratios of stock solutions required to obtain a mixed liquid flow having the pre-defined characteristics.

10 Claims, 4 Drawing Sheets

(51) Int. Cl.
   *G05D 11/13* (2006.01)
   *B01F 15/00* (2006.01)

(56) References Cited

U.S. PATENT DOCUMENTS

| | | | | |
|---|---|---|---|---|
| 4,500,500 | A * | 2/1985 | Paalman et al. | 423/224 |
| 5,112,949 | A * | 5/1992 | Vukovich | 530/380 |
| 5,284,174 | A | 2/1994 | Norman | |
| 5,992,437 | A * | 11/1999 | Takasaki et al. | 137/3 |
| 6,221,250 | B1 * | 4/2001 | Stafstrom | 210/656 |
| 6,224,778 | B1 * | 5/2001 | Peltzer | 210/739 |
| 7,138,051 | B2 * | 11/2006 | De Lamotte | 210/198.2 |
| 7,344,297 | B2 * | 3/2008 | Urquhart | 366/132 |
| 7,425,263 | B2 * | 9/2008 | Tsonev et al. | 210/198.2 |
| 7,871,249 | B2 * | 1/2011 | Urquhart et al. | 417/68 |
| 7,980,753 | B2 * | 7/2011 | Urquhart et al. | 366/132 |
| 2005/0029170 | A1 * | 2/2005 | Urquhart et al. | 210/96.1 |
| 2006/0035381 | A1 | 2/2006 | Bary et al. | |
| 2008/0053830 | A1 * | 3/2008 | Tsonev et al. | 204/661 |
| 2008/0279038 | A1 | 11/2008 | Bellafiore et al. | |
| 2009/0273203 | A1 * | 11/2009 | Adams | 296/184.1 |

FOREIGN PATENT DOCUMENTS

| | | |
|---|---|---|
| WO | WO 2004/103519 | 12/2004 |
| WO | WO 2005/025726 | 3/2005 |
| WO | WO 2007/008764 | 1/2007 |

* cited by examiner

METHOD AND SYSTEM FOR PREPARATION OF LIQUID MIXTURES

CROSS-REFERENCE TO RELATED APPLICATIONS

This application is a filing under 35 U.S.C. 371 of international application number PCT/SE2010/051023, filed Sep. 23, 2010, published on Mar. 31, 2011 as WO 2011/037530, which claims priority to application number 0950703-9 filed in Sweden on Sep. 25, 2009.

FIELD OF THE INVENTION

The present invention relates to the preparation of liquid mixtures, and more particularly to the preparation of liquid mixtures having pre-defined characteristics.

BACKGROUND OF THE INVENTION

In many cases it is important to obtain liquids of precisely known composition and/or other characteristics, such as pH, ionic strength, viscosity, density etc. It is further not uncommon that the composition of the liquid should not only be at each moment precisely known and controlled, but also should vary with time in a precise and controlled manner.

Such liquids are usually obtained by mixing or blending two or more liquids with each other, typically using a blending system, usually an on-site blending system, which may provide for both isocratic and gradient blending modes (step gradient and linear gradient).

One application where the composition of liquids is of utmost importance is in the field of liquid chromatography, when buffers having a specified pH and optionally also ionic strength are utilized, the pH and ionic strength of the eluent being the two most important parameters that control selectivity of protein separations in chromatography, such as on ion exchange resins. Another such application is filtration.

US 2008/0279038 A1 discloses a blending system for blending three liquids, a feed liquid and first and second adjusting liquids, using a continuous mode of operation. The feed liquid is, for example, water and the adjusting liquids may be a salt concentrated solution and alcohol, respectively. The liquids are mixed in a recirculation loop. The conductivity of the recirculated solution is sensed by a conductivity sensor communicating with a system controller which controls the valves and pumps of the system. A near infrared (NIR) sensor detects the alcohol concentration. When the target conductivity and the alcohol concentration levels have been attained, the output of the loop is delivered to the process. The salt concentrate solution and alcohol addition rates continue to be based on feedback control from the conductivity sensor and NIR sensor.

A different approach to liquid blending is to determine the exact relative component proportions or ratios in which liquids are to be blended to obtain a desired liquid mixture having the pre-defined characteristics, typically using an appropriate algorithm, and then produce a liquid mixture flow by feeding the different liquids by a metering system in the predetermined ratios.

U.S. Pat. No. 6,221,250 B1 discloses an apparatus for liquid chromatography comprising an on-line metering device capable of feeding into a chromatographic separation device an eluent of one or more buffering species, an acid or a base, optionally a salt, and a solvent, wherein the metering device calculates, by the use of an approximation of the Debye-Hückel equation, the relative proportions of the components required to obtain an eluent of a selected pH at a given salt concentration. This is accomplished by an iterative procedure where the different components are concomitantly varied in such a way as to take into account the interrelationship of the pH and the ionic strength in the liquid mixture.

However, the approximation of the Debye-Hückel equation used, similar to other methods using such approximations, suffers from poor accuracy at higher concentrations of buffer and/or salt.

A development of the calculation of the relative component proportions which overcomes the above-mentioned deficiency is disclosed in PCT application No. PCT/SE2009/050399 entitled "Preparation of liquid mixtures". A mixer control unit is provided to control the relative component proportions using the equation of Debye-Hückel, wherein the ion size a in the Debye-Hückel equation is determined as the weighted mean ion size of all species contributing to the ionic strength of the liquid mixture, wherein the ionic strength of each species is used as weighting parameter. In this improved method, which preferably is computer-implemented, the exact composition is first calculated and the liquid mixture, typically a buffer, is subsequently prepared in a single step. In one embodiment, the buffer definition is obtained in-line in a continuous process.

A disadvantage of the above-mentioned methods based on calculation of the component proportions is, however, that one must know the exact concentrations and/or other characteristics of the stock solutions at the time of use.

It is an object of the present invention to provide an improved method for preparing a liquid mixture flow having pre-defined characteristics and which may conveniently be automated, such as computer-implemented.

SUMMARY OF THE INVENTION

According to the present invention, the above-mentioned object as well as other objects and advantages are achieved by prior to mixing the stock solutions, separately subjecting a flow of each stock solution to a measurement of a characteristic of the stock solution, which characteristic can directly or indirectly be used for determining mixing ratios. The measurement values are then (i) evaluated to check if, or verify that, the measurement value obtained for a stock solution, or a value derived therefrom, is within acceptable pre-set limits (i.e. sufficiently accurate) for permitting mixing ratios according to a predetermined recipe to be used, and/or (ii) used for calculating proper mixing ratios of the stock solution flows for producing the desired liquid mixture flow.

In its broadest aspect, the present invention therefore provides a method of preparing a liquid flow having pre-defined characteristics by mixing liquid flows of at least two different component stock solutions with each other, which method comprises the steps of determining a selected property value for one or more of the stock solutions by sensing in a flow of each stock solution separately at least one characteristic related to the property value for the stock solution, and based on the determined property value or values, mixing the stock solution flows in mixing ratios giving the desired mixed liquid flow.

In one embodiment of this aspect of the invention, the method comprises verifying that the determined property value of each sensed stock solution is within a predetermined acceptable range for permitting predetermined mixing ratios of the stock solution flows to be used in order to obtain the desired mixed liquid flow, and then mixing the stock solution flows in the predetermined mixing ratios.

In another embodiment of this aspect of the invention, the method comprises using the determined property value or values of each sensed stock solution to calculate mixing ratios of the stock solutions flows which provide the desired mixed liquid flow, and mixing the stock solution flows in the calculated ratios.

The pre-defined characteristics of the mixed liquid flow are typically selected from concentration, pH and ionic strength, and the determined property value is preferably concentration.

For many applications, the sensed characteristic is selected from conductivity, pH, ultraviolet (UV) absorption and near infrared (NIR) absorbance.

In a preferred embodiment, the property value is concentration, the characteristic related to the property value is conductivity, and the concentration is determined from the conductivity via a predetermined relationship between conductivity and concentration.

In another aspect, the present invention provides a liquid mixture preparation system, which comprises (i) at least one outlet for mixed liquid and a plurality of inlets each of which is connected to a respective container for component stock solution; (ii) means for feeding a flow of each stock solution to the respective inlets; (iii) a control unit arranged to control the relative ratios of stock solutions supplied through the inlets to provide a mixed liquid flow having pre-defined characteristics at the outlet or outlets; and (iv) sensor means capable of sensing at least one characteristic of each stock solution flow, wherein the control unit is arranged to evaluate the characteristics sensed by the sensor means and provide relative mixing ratios of stock solutions required to obtain a mixed liquid flow having pre-defined characteristics.

In still another aspect, the present invention provides a separation system comprising a liquid mixture preparation system according to the second aspect above.

In a preferred embodiment, such a separation system omprises at least one of a liquid chromatography system and a filtration system.

Further preferred embodiments of the invention are set forth in the dependent claims.

A more complete understanding of the present invention, as well as further features and advantages thereof, will be obtained by reference to the following detailed description and the accompanying drawings.

DETAILED DESCRIPTION OF THE INVENTION

As mentioned above, the present invention relates to an improved method and system for providing a liquid flow having pre-defined characteristics. In brief, the desired liquid flow is prepared by combining liquid flows from two or more component stock solutions in relative proportions or ratios known or determined, such as calculated, to provide a liquid of the desired compositions and characteristics. Prior to performing the mixing ratio determination, the exact composition and/or other characteristics for each stock solution to be mixed are automatically determined on flows of the respective stock solutions, and the determined values are then either used to check that a stock solution is acceptable for mixing according to a predetermined recipe or needs to be adjusted; or used to calculate the necessary mixing ratios of the stock solutions for the desired liquid flow to be obtained.

While the method and system are generally applicable to the preparation of liquid mixture flows for various purposes, including isocratic and gradient liquid mixtures, the following detailed description will, by means of example only and not in any limiting sense, primarily be related to the fields of liquid chromatography and filtration, where pH and/or ionic strength of the liquid mixtures are of particular concern. Before describing the invention any further, the pH and ionic strength characteristics will first be generally addressed.

pH and pH Control

The pH value describes the degree of acidity in a solution and is defined as the negative logarithm of the activity of hydrogen ions (or protons). Most biological processes are affected by pH changes, the reason being that pH affects the interactions at molecular level and molecular conformations. For the same reason, changes in pH can be used to control chromatographic processes, for example in the production of biopharmaceuticals, such as monoclonal antibodies. As an example, pH is a crucial parameter for the interaction between monoclonal antibodies and protein A chromatographic media.

The key to pH control is the buffer. The buffer is a kind of molecule that is able to accept or donate hydrogen ion. By adding a large number of such molecules to a solution, pH control can be attained by effectively reducing the rate of pH change as a function of the amount of hydrogen or hydroxyl ions. This "buffer capacity" is proportional to the buffer concentration. It is also possible to control pH by deliberate combination of the buffer molecule in two different protonation states. Since macroscopic chemical reagents must be electrically neutral, those that work as buffers can be forced to different protonation states by the presence of the appropriate amount of counter ions. This may, for example, be obtained by combining a "weak acid" with a corresponding weak base. For environmental or human safety reasons, this is preferable to combining the weak acid with a strong base (like NaOH), or a weak base with a strong acid (like HCl).

A key parameter for a buffer substance is its $pK_a$ value which is the pH value at which 50% of the buffer molecules are in each of two different protonation states. Some buffer substances like phosphate and citrate have several $pK_a$ values (polyprotic buffers). The $pK_a$ values of a substance can shift dramatically when the conductivity increases, for instance by adding salt to the buffer solution. The knowledge of the magnitude of such shifts for different buffer systems at different salt concentrations can be used for accurate pH control.

Ionic Strength (or Conductivity)

Since buffer substances are weak electrolytes there is no simple model that can relate the conductivity as a function of the concentration. Contributions to the conductivity of a buffer arise from different components which correspond to different protonation steps. The exact proportions of the different states depend upon the equilibrium and thus vary with the pH etc. An important contribution to the conductivity comes from strong electrolytes, for instance $Na^+$ and $Cl^-$ ions, especially at higher salt concentrations. Conductivity control is important because the conductivity (or the ion strength) also can effect intermolecular interactions and can therefore be used to control the chromatographic processes for biopharmaceutical production, especially such using ion exchange chromatography or hydrophobic interaction chromatography. Adding salts like NaCl or $Na_2SO_4$ is a cost effective way to increase the conductivity of a solution. The conductivity is also a good measure of the concentration of a solution even if the relation between the two is not trivial. Knowledge of this relation for instance obtained empirically can be used to determine if the concentration or the stock solution is correct.

Figure 1:
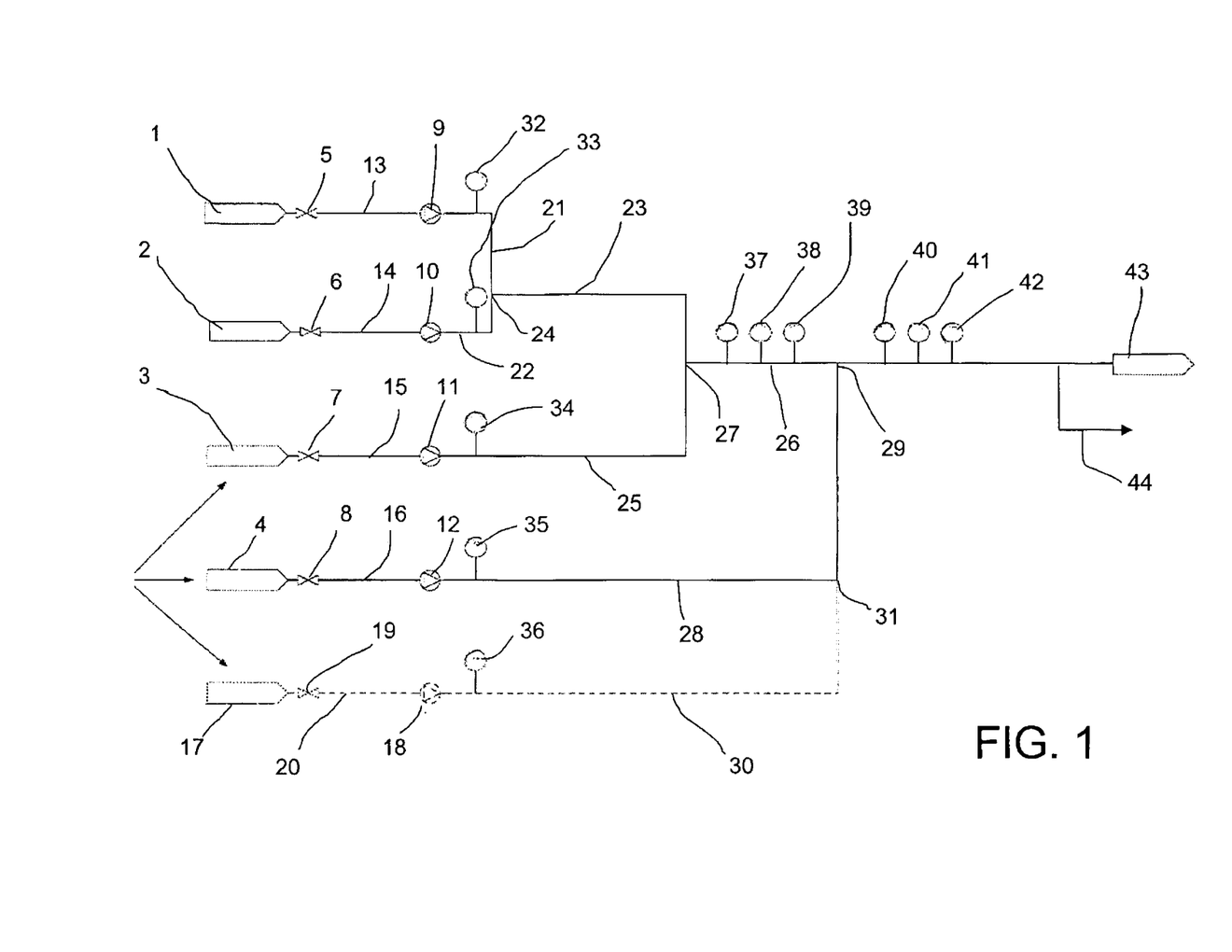
FIG. 1 is a schematic diagram of a liquid blending system which may be used in the method of the present invention.

Turning now to the invention, FIG. 1 shows in diagrammatic form a blending system or arrangement which can be used for preparing buffers or other liquids having pre-defined characteristics, for example for use in chromatography, in accordance with the method of the present invention.

The blending system includes a plurality of inlets, here four inlets 1-4, for stock solutions, or feedstocks, supplied from corresponding containers or tanks (not shown) and intended to be mixed in the system. (For simplicity, the same reference numerals 1-4 are also used for the corresponding stock solutions.) The feedstock inlets 1-4 are via valves 5-8 connected to respective pumps 9-12 through conduits 13-16. An optional feedstock inlet is indicated at 17, which is connected to a pump 18 via a valve 19 and a conduit 20.

The outlets of pumps 9 and 10 are coupled via conduits 21 and 22 to a conduit 23 at a T-junction 24. The outlet of pump 11 is connected to a conduit 25 which together with conduit 23 is coupled to a conduit 26 at a T-junction 27.

The outlet of pump 12 is connected to a conduit 28 which joins conduit 26 at a T-junction 29. The outlet of the optional pump 18 is via a conduit 30 coupled to conduit 28 at a T-junction 31.

In-line flow sensors 32-36 are provided downstream of each pump 9-12 in their respective outflow conduits 21, 22, 25, 28 and 30.

Conduit 26 is provided with first and second sets of in-line sensors for sensing different desired liquid characteristics, the first set upstream and the second set downstream of the T-junction 29. In the illustrated case, the first and second sensor sets each includes three sensors 37-39 and 40-42, respectively. For instance, sensors 37 and 40 may be conductivity sensors, sensors 38 and 41 may be UV (or near infrared) sensors, and sensors 39 and 42 may be pH sensors.

The pumps may, depending on the flow volumes and rates, be selected from, for example, peristaltic pumps, piston pumps and diaphragm pumps. Typically, diaphragm pumps are used.

When blending feedstocks supplied through the different inlets 1-4 (and 17), the feedstock flows from inlets 1 and 2 are first mixed via T-junction 24, and the resulting flow in conduit 23 is then mixed at T-junction 27 with the flow of feedstock from inlet 3 in conduit 25. Finally, the resulting flow in conduit 26 is mixed at T-junction 29 with the feedstock flow from inlet 4 in conduit 28 to provide the desired liquid mixture, e.g. a buffer, at outlet 43. Optionally, more than one outlet may be provided as is indicated at 44 in FIG. 1.

The illustrated blending system configuration is only exemplary, and various other system configurations are, of course, possible and readily apparent to a person skilled in the art. This concerns, for instance, the conduit configuration as well as the means for causing the liquid flows. While in the illustrated case pumps are used for driving the liquids, other means may be used for liquid feeding, such as suction (e.g. pump generated) or pressurized liquid tanks.

Using the system shown in FIG. 1 and described above, two, three, four or optionally more different feedstocks may be blended to form a liquid mixture having pre-defined characteristics. The relative proportions of the different feedstocks to be blended are typically obtained from a predetermined recipe (i.e. pre-set mixing ratios) known to produce the desired liquid mixture if the feedstock are blended in the proportions according to the recipe. The different feedstock flows are sensed by the flow sensors 32, 33, 34, 35 (and 36), and the sensor signals are fed to appropriate control means (not shown), which regulate the respective pumps 9-12 to provide the desired mixing ratios of the feedstock flows. This may be referred to as "flow feedback control".

For example, for preparing a buffer having a desired ionic strength and pH, the feedstock supplied to inlet 1 may be water (typically water for injection—WFI), the feedstock supplied to inlet 2 may be a salt solution (typically sodium chloride or ammonium sulphate), the feedstock supplied to inlet 3 may be an acidic buffer substance, and the feedstock supplied to inlet 4 may be a basic buffer substance.

This order of mixing the different feedstocks is only exemplary and may be varied, depending inter alia on the miscibilities of the liquids with each other, substance solubilities, etc.

Optionally, several different feedstock tanks may be provided for each inlet 1-4 (and 17). For instance, with reference to the example above, several tanks with solutions of different salts (or salt mixtures) and/or salt solutions at different salt concentrations may be provided for inlet 2. Likewise, several tanks containing different acid buffer substances and/or one buffer substance at different concentrations may be provided for inlet 3, and the same applies to the supply of basic buffer substance at inlet 4.

As mentioned above, a buffer may be prepared from (i) a weak acid and a weak base, or (ii) a weak acid and strong base, or a weak base and a strong acid. Preferably, the buffer component properties should not exhibit the same value at two different concentrations in the relevant range.

Exemplary buffers that may be produced using the liquid blending system include phosphate, acetate, citrate, tris and bis-tris buffers, just to mention a few.

Alternatively, one or more of the inlets 3, 4 and 17 may be supplied with organic solvents rather than acid and/or base. Exemplary such solvents include methanol, ethanol, and acetonitrile.

For calculating a blending recipe for the preparation of a salt-containing liquid mixture having a desired pH, such as a chromatography buffer, from feedstocks of known concentrations, and optionally of known pH and/or ion strength, it is as mentioned above necessary to take into account the interrelationship of the ionic strength and the pH of the mixture.

For lower concentrations of buffer and/or salt, the method and apparatus described in U.S. Pat. No. 6,221,250 (the full disclosure of which is incorporated by reference herein) may be used, which is based on an iterative calculation procedure using a modified equation of Debye-Hückel to determine the variable proportions of the components, and wherein an approximation of the ion size parameter in the Debye-Hückel equation is used. The proportions of the components are concomitantly varied in such a way as to take into account the interrelationship of the pH and the ionic strength of the mixture to obtain at each moment a pre-selected pH of the mixture.

An improvement of that method and apparatus which can be used also for high buffer and salt concentrations is described in International application PCT/SE2009/050399 entitled "Preparation of liquid mixtures" (the full disclosure of which is incorporated by reference herein). Here the relative component proportions are determined using the equation of Debye-Hückel:

$$-\log \phi = (AZ^2 I^{0.5})/(1+0.33*10^8 \alpha I^{0.5})$$

wherein A is a constant, or rather a temperature dependent parameter ~0.51 (A can accurately be calculated as $A=0.4918+0.0007*T+0.000004*T^2$ where T is the temperature in degrees Celsius), Z is the charge of the ion, and the quantity $\alpha$, the radii of the hydrated ions (in Å), is the "mean distance of approach of the ions, positive or negative" (in the original paper of Debye and Hückel), and determining the ion size parameter $\alpha$ in the Debye-Hückel equation as the weighted mean ion size of all species contributing to the ionic strength of the liquid mixture, and wherein the ionic strength of each species is used as the weighting parameter. More particularly, the ion size parameter $\alpha$ of the Debye-Hückel equation is determined as $$a = \frac{\sum I_i a_i}{I}$$

wherein $I_i$ is the ionic strength and $\alpha_i$ the ion size parameter of species i, and I is the total ionic strength.

Many times, the ion size parameter in the Debye-Hückel equation may be approximated as $a=0.5*(mass)^{1/3}+shell$, where "shell" is typically fixed at a value in the range of 3.8-4.2, such as 4.0, for positively charged ionic species; and fixed at a value in the range of 0-0.2, such as 0, for negatively charged ionic species.

The iterative procedure for determining the mixing ratios comprises (i) determining the relative component proportions wherein the pre-defined ionic strength of the liquid mixture is addressed to the species according to a predefined distribution among the species; (ii) on the basis of the relative component proportions determined in (i), calculating the ionic strength of each species in the mixture; (iii) determining a new set of relative component proportions, taking account of the ionic strength calculated in (ii), and (iv) repeating steps (ii) and (iii) until a predetermined convergence criteria is met.

Any other method that can provide exact mixing ratios may, of course, also be used.

Using the system shown in FIG. 1 and a suitable control system, the recipe (i.e. the mixing ratios) for obtaining a desired liquid mixture may be programmed into the control means, which e.g. may comprise computer means and dedicated software, and the control means will then regulate the flows of the different feedstocks to obtain the required relative proportions of the flows, using feedback from the flow sensors in each pump outflow (i.e. flow feedback control).

The sensors 40-42 may also be used for monitoring that the desired characteristics of the liquid flow in conduit 26 are correct and stable, and the control system may be arranged to indicate any deviation therefrom, so that the liquid outflow from conduit 26 at outlet 43 (and 44) may optionally be stopped. Alternatively or additionally, feedback from the sensors may be used for fine adjustment of the liquid flow composition (i.e. the mixing ratios).

For the control of the preparation of a buffer or other liquid for a chromatography system, the software used for controlling the chromatography system, if any, may be used. An exemplary such software is the Unicorn™ control system (GE Healthcare Bio-Sciences AB, Uppsala, Sweden), which is based on a controller and I/O interface with a computer graphical user interface, being an integral part of the control system.

The stock solutions may be prepared manually or be provided by other means. The actual component concentration of a prepared stock solution may, however, differ from the intended or assumed concentration for various reasons. For example, the recipe for the preparation may by mistake not have been followed correctly, a stock solution may have changed during storage, stock solution in a non-stirred tank may exhibit a gradient of the component or components, etc.

To ensure that the correct (or sufficiently accurate) concentrations (or other characteristics) of the stock solutions are used when determining the mixing ratios, a measurement is performed on a flow of each stock solution separately prior to mixing the stock solutions.

Figure 2:
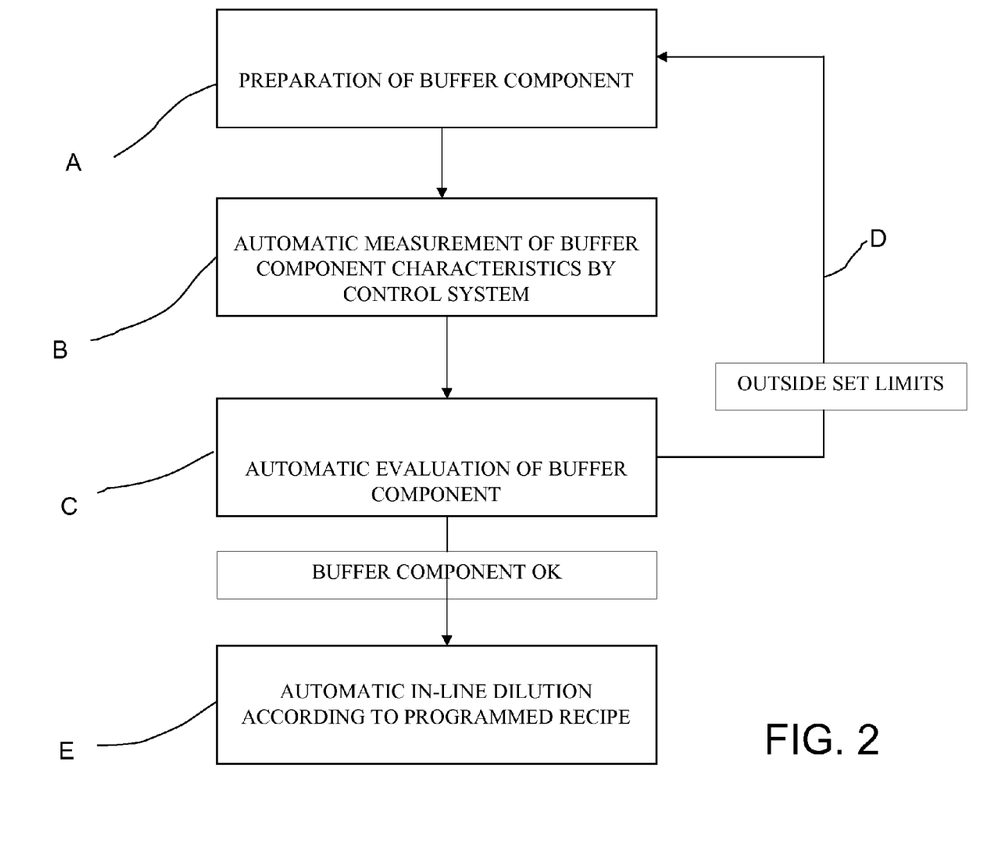
FIG. 2 is a schematic block diagram showing the different steps in one embodiment of the method according to the present invention.
Figure 3:
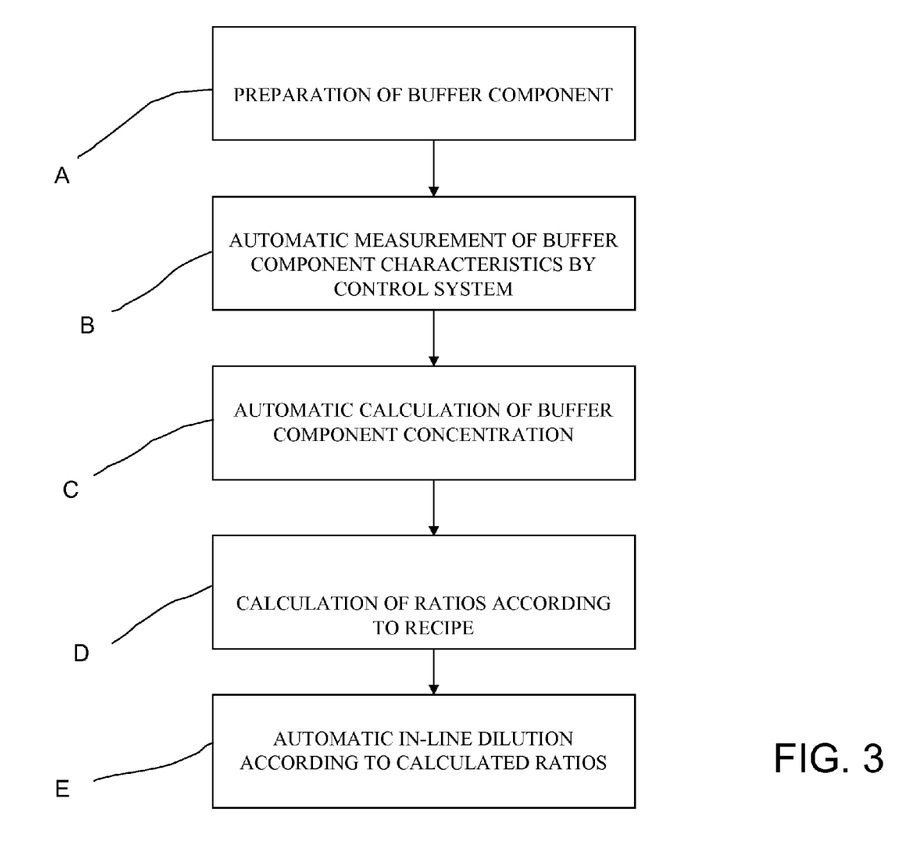
FIG. 3 is a schematic block diagram showing the different steps in another embodiment of the method according to the present invention.

FIGS. 2 and 3 show in flow diagram form two alternative embodiments of the method of the present invention which include such a check or measurement of the stock solution characteristics. The different steps for preparing a liquid mixture having pre-defined characteristics according to each embodiment will now be described applied to the system shown in FIG. 1. For illustration only and no limitation, it is assumed that a buffer having a desired ionic strength and pH should be prepared from pre-defined stock solutions of (i) an acid, (ii) a base, (iii) a salt and (iv) water.

For the pre-defined stock solutions, the control system has programmed or determines the relative proportions in which the stock solutions must be mixed to obtain the desired liquid mixture (buffer), typically by a using a recipe or an appropriate algorithm as described above. These data are then used to set control parameters for the pumps etc in the system in FIG. 1.

In the first embodiment, outlined in FIG. 2, the measurements on the stock solution flows are used to determine if the concentrations of the different stock solutions are within an acceptable pre-determined range, i.e. within pre-set limits considered as acceptable for using the mixing ratios for the stock solutions given in an existing recipe. The following steps are performed.

A. Stock solutions (buffer components) are prepared (e.g. manually) according to predetermined formulas. With reference to FIG. 1, it is thus assumed that the stock solution for inlet 1 is water, the stock solution for inlet 2 is a salt solution, the stock solution for inlet 3 is an acidic buffering species and the stock solution for inlet 4 is a basic buffering species.

B. Before starting the actual mixing procedure, an automatic measurement is performed on each stock solution to check whether it in fact has the presumed concentration and/or other characteristic. Generally, concentrations for buffer and salt solutions may be measured through conductivity measurements by using pre-prepared graphs plotting the conductivity as a function of the concentration of the stock solutions. Alternatively, concentrations may be measured through UV or NIR measurements.

Specifically, with reference to FIG. 1, the control system sequentially activates each pump 9-12 to pump a flow of each stock solution 1-4 into conduit 26, one or optionally more characteristics of each stock solution being sensed by a sensor of the sensor set 40-42. For example, conductivities may be measured for stock solutions 1 (water) and 2 (salt solution) by the conductivity sensor 40, whereas conductivities and/or pH for stock solutions 3 (acid) and 4 (base) may be measured by conductivity sensor 40 and pH sensor 42. Should a stock solution containing an organic solvent be used, its concentration may be measured via UV sensor 41.

C. The respective measured sensor data for the stock solutions are fed to the control system which, when relevant after transforming conductivity data into concentration, evaluates these data to provide correct values for the characteristic(s)

for each stock solution, and then determines if the obtained values are within pre-set limits considered as acceptable for preparing the desired buffer according to an existing recipe of mixing ratios for stock solutions of predetermined concentrations.

D. If a determined correct value or values for a stock solution is outside the set limits, the stock solution in question is adjusted, or a new stock solution is prepared, and steps A-C above are then repeated for that stock solution.

E. If a determined correct value or values for a stock solution is within the set limits, the control system then activates valves and pumps of the system in FIG. 1 to mix the stock solution flows in the relative proportions or ratios which will provide an outflow at 43 from conduit 26 consisting of the desired buffer having the pre-defined pH and ionic strength. Flow control may be achieved by controlling the pumps and/or valves, as is customary in the art, via feedback from the flow sensors.

In the alternative embodiment, shown in FIG. 3, the results of the measurements on the stock solution flows are used to calculate the mixing ratios therefrom according to an equations (s) or calculation recipe. The following steps are performed.

A. This step is the same as for the embodiment in FIG. 2 described above, i.e. stock solutions of the buffer components are provided.

B. This step is the same as for the embodiment in FIG. 2 described above, i.e. measurements of stock solution characteristics are performed on flows thereof.

C. The respective measured sensor data for the stock solutions are fed to the control system which, when relevant after transforming conductivity data into concentration, evaluates these data to provide correct values for the characteristic(s) for each stock solution.

D. The control system then automatically calculates from the determined correct values the necessary mixing ratios for obtaining a buffer having the desired characteristics, e.g. using a predetermined equation (s) or calculation recipe.

E. The control system then activates valves and pumps of the system in FIG. 1 to mix stock solution flows in the calculated relative proportions or ratios which will provide an outflow at 43 from conduit 26 consisting of the desired buffer having the pre-defined pH and ionic strength.

Optionally, the two alternative approaches described above may be mixed, i.e. the first alternative (FIG. 2) may be used for one or more stock solutions, and the second alternative (FIG. 3) may be used for the remaining stock solutions.

In a variant approach, preliminary mixing ratios may be calculated based on assumed property values for the stock solutions, and the sensor-based values are then used to adjust the preliminary mixing ratios to final mixing ratios.

As mentioned above, the sensors 40-42 (and optionally 37-39) will monitor the produced buffer flow and indicate any deviation from the desired characteristics of the liquid flow, and the control system may, if desired, be arranged to compensate for changes in e.g. temperature and salt concentration through feedback control.

Optionally, sensors may be provided for monitoring the stock solution characteristics and updating the mixing ratios continuously.

At least in come cases, it may be desired to use multiple blending systems, i.e. two or more blending modules, of the type described above to permit, for instance in chromatography, while a first liquid mixture flow is provided by a first blending module, that a second blending module can be prepared for providing a second liquid mixture flow so that it may be supplied substantially without any interruption when the liquid mixture is to be used.

The blending method and system of the present invention, embodiments of which have been described above, may advantageously be used for delivering in-line buffers and other liquids to a separation system of the type disclosed in our co-pending application "Separation system and method" filed concomitantly herewith.

In the following Example, the preparation of a buffer will be described.

EXAMPLE

Preparation of 30 mM Phosphate Buffer, pH 6.5

0.4 M stock solutions of $Na_2HPO_4$ and $NaH_2PO_4$ were provided. Mixing ratios were calculated by solving equilibrium equations, taking into consideration the shift in the $pK_a$ values due to the ionic strength, basically as described further above, using a proprietary algorithm (GE Healthcare Bio-Sciences AB, Uppsala, Sweden).

Figure 4:
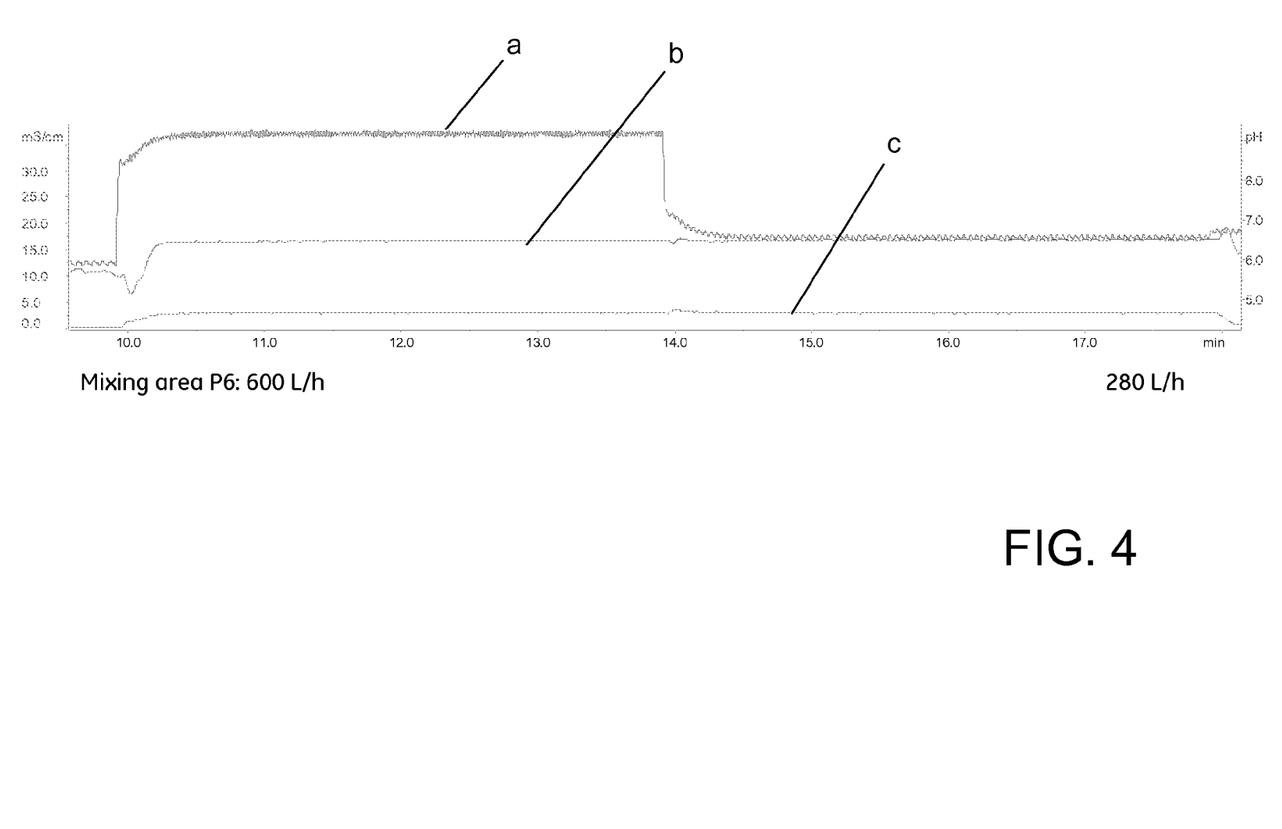
FIG. 4 is a set of graphs showing the variation of the total flow, pH, and conductivity, respectively, during the mixing of two liquid flows at two different flow rates.

A liquid blending system, basically corresponding to that in FIG. 1 (using diaphragm pumps) was then used to prepare a liquid flow of the desired buffer, having the mixing ratios programmed into the control system (Unicorn™), at two different flow rates, 600 L/h and 280 L/h, respectively. The flow, conductivity and pH of the prepared buffer were continuously monitored. The results are shown in FIG. 4, where curve a is the combined flow, curve b is pH, and curve c is the conductivity. As apparent from the graphs, efficient mixing producing a stable buffer flow with the desired pH and conductivity was obtained in a short time for both flow rates.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method of preparing a buffer solution using a plurality of stock solutions, the buffer solution having predetermined characteristics, the method executed by a flow control system, and the method comprising:

combining the plurality of stock solutions to obtain the buffer solution, the combining including:

sensing a current value of a property of a first stock solution, a current value of a property of a second stock solution, and a current value of a property of a third stock solution;

determining whether the sensed current value for the first stock solution is within a predetermined range;

adjusting the current value for the first stock solution to within the predetermined range, when the sensed current value is not in the predetermined range, by flow-feedback of the first stock solution and by continuously sensing the current value for the first stock solution and determining whether the sensed current value for the first stock solution is within the predetermined range;

calculating a relative proportion for each one of the second stock solution and the third stock solution based on (i) the sensed current value of the property for the second stock solution, (ii) the sensed current value of the property for the third stock solution, and (iii) the predetermined characteristics of the buffer;

adjusting, in response to the calculating and according to the respective relative proportions, flow rates of the second stock solution and the third stock solution; and mixing the first stock solution, the second stock solution, and the third stock solution to obtain the buffer solution.

2. The method of claim 1, wherein the current value for one of the first, the second, and the third stock solution is a measure of concentration.

3. The method of claim 1, wherein the property of one of the first, the second, and second the third stock solution is selected from conductivity, pH, UV absorbance and NIR absorbance.

4. The method of claim 3, wherein the sensed current value for one of the first, the second, and the third stock solution is obtained by sensing one of conductivity, pH, UV, absorbance, and NIR absorbance.

5. The method of claim 1, wherein said predetermined characteristics of the buffer solution are selected from concentration, pH, ionic strength and conductivity.

6. The method of claim 1, wherein the sensed current value for the first stock solution is selected from the group consisting of conductivity, pH, UV absorbance and NIR absorbance.

7. The method of claim 1, wherein the first stock solution is an acid and the second stock solution is a base or vice versa.

8. An apparatus for preparing a buffer having predetermined characteristics, the apparatus comprising:
   a flow system configured to provide a first stock solution, a second stock solution, and a third stock solution;
   a first sensor configured to sense a first current value of a property of the first stock solution, a second sensor configured to sense a second current value of a property of the second stock solution, and a third sensor configured to sense a third current value of a property of the third stock solution;
   a control unit programmed to:
   (i) determine whether the sensed first current value is within a predetermined range;
   (ii) adjust the first current value to within the predetermined range, when the sensed first current value is not in the predetermined range, by flow-feedback of the first stock solution and by continuously sensing the first current value and determining whether the sensed first current value is within the predetermined range;
   (iii) perform a calculation of a relative proportion for each one of the second stock solution and the third stock solution based on the sensed second current value, the sensed third current value, and the predetermined characteristics of the buffer; and
   (iv) adjust, in response to the calculation and according to the respective relative proportions, flow rates of the second stock solution and the third stock solution; and
   (v) mix the first, second, and third stock solutions to obtain the buffer.

9. The system of claim 8, wherein the apparatus is a separation system.

10. The apparatus of claim 9, wherein the separation system includes one of a liquid chromatography system and a filtration system.

* * * * *